(12) United States Patent
Krammer et al.

(10) Patent No.: US 6,485,929 B1
(45) Date of Patent: Nov. 26, 2002

(54) METHOD FOR INHIBITING CD95-INDEPENDENT APOPTOSIS IN AIDS

(75) Inventors: Peter Krammer, Heidelberg (DE); Christina Berndt, München (DE)

(73) Assignee: Deutsches Krebsforschungzentrum Stiftung des offentlichen Rechts, Heidelberg (DE)

( * ) Notice: Subject to any disclaimer, the term of this patent is extended or adjusted under 35 U.S.C. 154(b) by 0 days.

(21) Appl. No.: 09/600,522

(22) PCT Filed: Jan. 15, 1999

(86) PCT No.: PCT/DE99/00109

§ 371 (c)(1),
(2), (4) Date: Oct. 11, 2000

(87) PCT Pub. No.: WO99/36091

PCT Pub. Date: Jul. 22, 1999

(30) Foreign Application Priority Data

Jan. 15, 1998 (DE) .......................................... 198 01 265

(51) Int. Cl.[7] .............................. C12Q 1/06; C12Q 1/70

(52) U.S. Cl. ............................................. 435/39; 435/5

(58) Field of Search ........................................ 435/5, 39

(56) References Cited

PUBLICATIONS

Radrizzani, et al., "IL–12 Inhibits Apoptosis Induced In A Human Th1 Clone By gp120/CD4 Cross–Linking and CD3/TCR Activation or By IL–2 Deprivation", *Cell. Immunol.*, 161:14–21 (Mar., 1995).

Corbeil, J. and Reichman, D.D., "Productive Infection and Subsequent Interaction of CD4+T Cells", *Journal of General Virology*, 76:681–690, (1995).

Berndt, C. et al., "CXCR4 and CD4 Mediate A Rapid CD95–Independent Cell Death In CD4+T Cells", *Proceedings of the National Academy of Sciences of USA*, 95:12556–12561, (Oct., 1998).

Primary Examiner—Hankyel T. Park
(74) Attorney, Agent, or Firm—Albert P. Halluin; Viola T. Kung; Howrey, Simon, Arnold & White, LLP

(57) ABSTRACT

The invention relates to a method for inhibiting CD95-independent apoptosis, comprising the following steps:
(a) blocking the bonding of HIV-1 gp120 on receptors CD4 and/or CXCR4 or of a factor competing for this bonding, and/or
(b) inhibiting the signal path induced by the bonding of (a).

The invention also relates to a system for identifying substances which can be utilized for inhibiting CD95-independent apoptosis.

10 Claims, 2 Drawing Sheets

METHOD FOR INHIBITING CD95-INDEPENDENT APOPTOSIS IN AIDS

FIELD OF THE INVENTION

The present invention relates to a method of inhibiting CD95-independent apoptosis, in particular in the case of AIDS. The invention also relates to a system for identifying substances which can be used for inhibiting CD95-independent apoptosis.

BACKGROUND OF THE INVENTION

AIDS is characterized by a depletion of $CD4^+T$ cells and a dysfunction of the immune system. Previous data refer to the fact that a depletion occurs because the CD95 receptor is activated by the CD95 ligand present in increased amount in the presence of the glycoprotein gp120 of HIV, so that apoptosis, i.e. programmed cell death, is induced in $CD4^+T$ cells. This apoptosis is referred to as CD95-mediated apoptosis.

Experiments have been made to prevent the depletion of $CD4^+T$ cells in the case of AIDS. For this purpose, methods were carried out with substances which block the bonding of the CD95 ligand to the CD95 receptor. However, these methods did not fully prevent the depletion of $CD4^+T$ cells.

Therefore, it is the object of the present invention to provide a method by which the depletion of $CD4^+T$ cells in the case of AIDS can be investigated and optionally be prevented.

According to the invention this is achieved by the subject matters defined in the claims.

SUMMARY OF THE INVENTION

The subject matter of the present invention relates to a method of inhibiting CD95-independent apoptosis, the method comprising the steps of:
(a) blocking the bonding of HIV-1 gp120 to receptors CD4 and/or CXCR4 and blocking a factor competing for this bonding, respectively, and/or
(b) inhibiting the signal path induced by the bonding of (a).

DETAILED DESCRIPTION OF THE INVENTION

Figure 1:
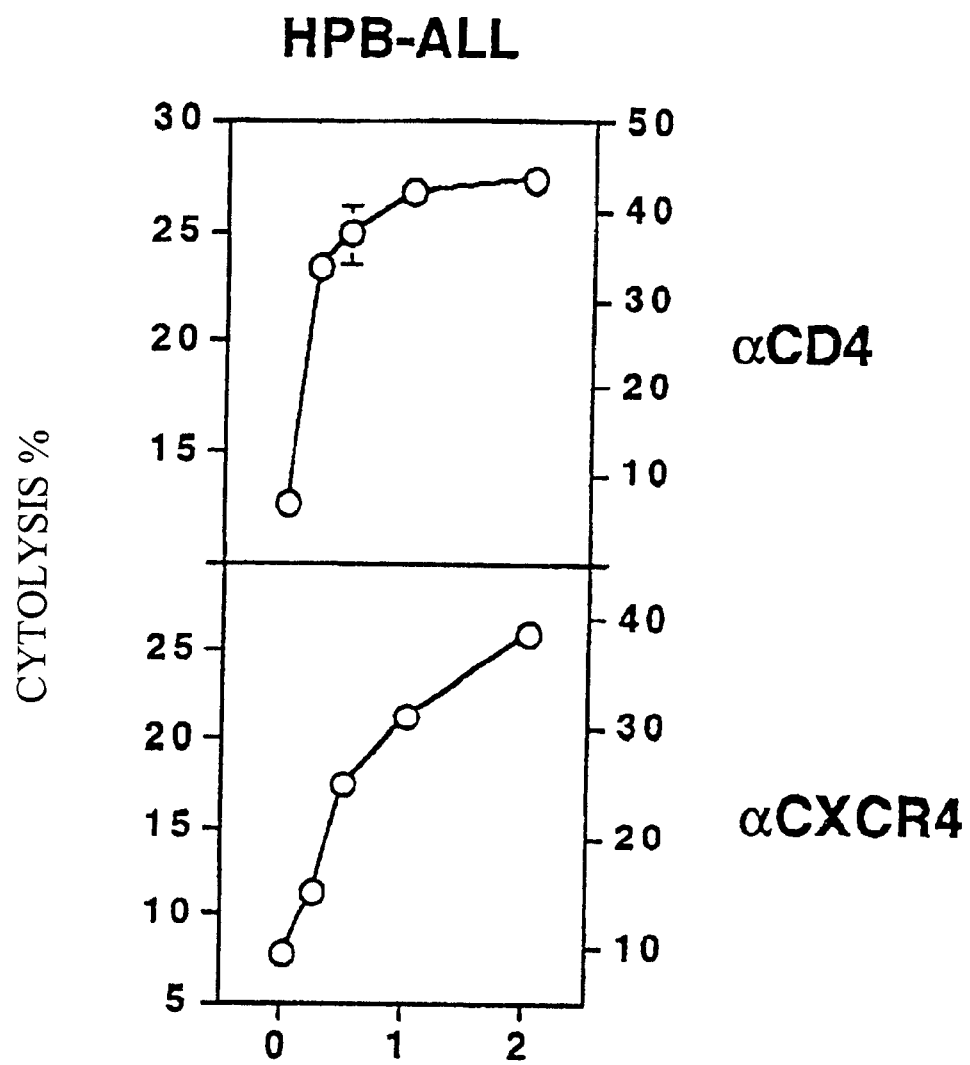
FIG. 1 shows the percent of cell death of HPB-ALL cells when incubated with anti-CD4 antibody or CXCR4 antibody.

The present invention is based on the applicant's insight that not only CD95-mediated apoptosis but also CD95-independent apoptosis may occur in cells. He found that the CD95-independent apoptosis is induced e.g. in that the glycoprotein gp120 of HIV-1 binds to the receptors CD4 and/or CXCR4. These receptors are present in different cells. The applicant also realized that the receptors CD4 and CXCR4 can also be activated by other factors through which apoptosis is induced. These factors are in particular those competing with HIV-1 gp120 for the bonding to receptors CD4 and CXCR4. Furthermore, the applicant found that the CD95-independent apoptosis differs from the CD95-mediated apoptosis as regards various properties. Some of these properties are listed in below Table 1.

TABLE 1

|  | CD95-mediated apoptosis | CD95-independent apoptosis via CD4 | CD95-independent apoptosis via CXCR4 |
| --- | --- | --- | --- |
| DNA breakdown | + | − | − |
| Kinetics | ~12 H | ~15 min | ~15 min |
| Changes in FSC/SSC | + | + | + |
| Loss of membrane asymmetry | + | + | + |
| Chromatin condensation | + | + | + |
| $\Delta\Psi_m$ | + | + | + |
| 7-AAD-test positive[+)] | + | + | ND[')] |
| Inhibition by zVAD-fmk | + | − | − |
| Caspase-3 cleavage | + | − | − |
| Caspase-8 cleavage | + | − | − |
| PARP cleavage | + | − | − |

[+)]Apoptotic cells can be differentiated from necrotic cells by staining using the fluorescent dye 7-amino-actinomycin D (7-AAD).
[')]not determined According to the invention the above insights are used for a method by which CD95-independent apoptosis can be inhibited. Such a method comprises the steps of:
(a) blocking the bonding of HIV-1 gp120 to receptors CD4 and/or CXCR4 and blocking a factor competing for this bonding, respectively, and/or
(b) inhibiting the signal path induced by the bonding of (a).

The expression "receptors CD4 and/or CXCR4" refers to the fact that these receptors can be present in cells of any kind and origin. In particular, these may be cells in which CD4 and/or CXCR4 occur by nature. Examples of such cells are $CD4^+/CXCR4^+T$ cells, such as HPB-ALL cells. The cells may also be cells in which CD4 and/or CXCR4 does not occur by nature but which have been introduced artificially. Examples of such cells are lymphoblastoid B cells, such as BJAB cells. Furthermore, the expression "receptors CD4 and/or CXCR4" also comprises those portions of these receptors to which HIV-1 gp120 or a factor competing therewith can bind.

The expression "a factor competing for the bonding" comprises any factor which can compete with HIV-1 gp120 for the bonding to receptors CD4 and/or CXCR4. In particular, the factor may be an anti-CD4 antibody, such as HP2/6 (Carrera, University of Madrid) or IOT4A (Immunotech). The factor may also be an anti-CXCR4 antibody, such as 12G5 (R+D Systems). Moreover, the factor may be another HIV protein, e.g. the glycoprotein gp160. An above HIV protein may originate from any HIV strain, in particular from HIV-1 or HIV-2. Furthermore, the factor may be a protein which is derived from a HIV protein. Such a protein can comprise e.g. the region responsible in HIV proteins for the binding to the receptors CD4 and CXCR4.

The expression "blocking the bonding" comprises any kind and any means by which the bonding of HIV-1 gp120 to receptors CD4 and/or CXCR4 and a factor competing for this bonding, respectively, can be blocked. In particular, the means can be the natural ligand of CD4, such as an MHC molecule. The means can also be the natural ligand of CXCR4, such as SDF-1α. It may be favorable for the natural ligands of CD4 and CXCR4 to be used jointly.

The expression "inhibition of the signal path" comprises any kind and any means by which the signal path can be inhibited, which is induced by the bonding of HIV-1 gp120 to the receptors CD4 and/or CXCR4 and a factor competing for this bonding, respectively. In particular, the means may be one by which the loss of membrane asymmetry can be prevented. The means may also be one by which the condensation of chromatin can be prevented.

According to the invention there is also provided a system by which CD95-independent apoptosis can be investigated. Furthermore, substances can be identified by this system, which are suitable for the inhibition of CD95-independent apoptosis. Such a system comprises cells which are CD4+ and/or CXCR4+, and HIV-1 gp120 and a factor which competes with HIV-1 gp120 for the bonding to CD4+ and/or CXCR4+, respectively, as well as optionally a substance whose inhibitory effect shall be determined on the bonding of HIV-1 gp120 to the receptors CD4 and/or CXCR4 or a factor competing for this bonding and on the signal path induced by this binding, respectively. It may be favorable for the system to also contain a substance whose inhibitory effect is known. The above statements apply correspondingly to such substances as well as other components of the system.

By means of the present invention it is possible to investigate and influence CD95-independent apoptosis. In particular, it is possible to inhibit CD95-independent apoptosis. On the other hand, the invention also refers to the possiblities of inducing CD95-independent apoptosis. Such possibilities will result inter alia from the use of factors which compete with the bonding of HIV-1 gp120 to receptors CD4 and/or CXCR4. Such factors are in particular antibodies directed against CD4 and CXCR4, respectively. Furthermore, the present invention enables to identify substances which can influence, in particular inhibit, CD95-independent apoptosis.

Therefore, the present invention represents the possibility of inhibiting and inducing, respectively, CD95-independent apoptosis. Thus, the present invention provides a means for preventing the depletion of CD4+T cells in the case of AIDS. Furthermore, the present invention represents a means for inducing CD95-independent apoptosis in well-calculated fashion, which is of significance in particular for combating tumor cells.

EXAMPLES

The invention is explained by the below example.

Example

Induction of CD95-independent Apoptosis and its Inhibition
I. Induction of CD95-independent Apoptosis
(a) CD4+/CXCR4+ cells (HPB-ALL cells) are used. HPB-ALL cells are CD95−, i.e. no CD95-mediated apoptosis occurs in them.

1×10$^5$ HPB-ALL cells are incubated with 5 μg/ml mouse anti-CD4 antibody (HP2/6) and mouse anti CXCR4 antibody (12G5), respectively, at 37° C. for 15 minutes. Then, the bound antibodies are reacted with sheep anti-mouse antibodies (100 μg/ml, Boehringer). Apoptosis detection is carried out in which an FSC/SSC analysis is run in an FACScan cytometer at various times (cf. FIG. 1).

It shows that the antibodies anti-CD4 and anti-CXCR4, respectively, can each induce CD95-independent apoptosis.

(b) CD4−/CXCR4− cells (BJAB cells) are used. The receptors CD4 and CXCR4 are introduced into these cells by transfecting DNA constructs coding for the receptors into the cells and then expressing them.

Figure 2:
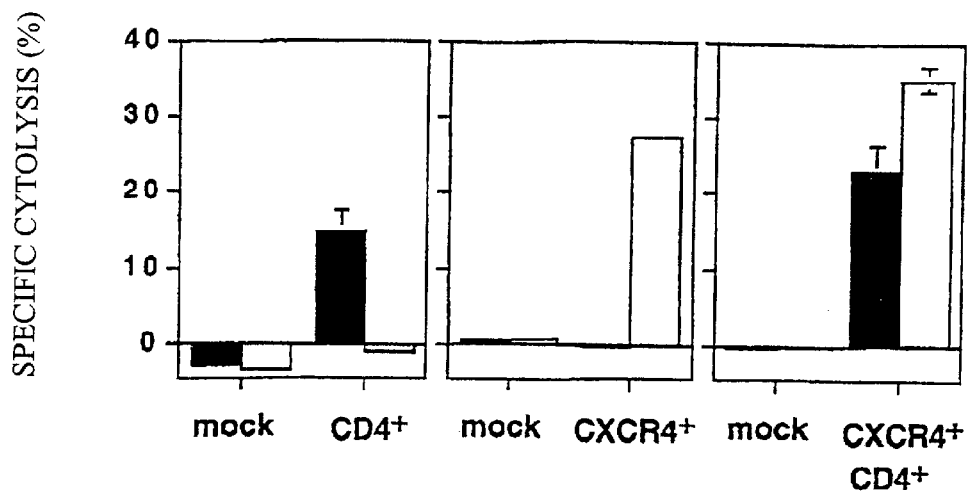
FIG. 2 shows the percent of specific cell death of BJAB cells, which express CD4, CXCR4 or CD4 and CXCR4.
Figure 3:
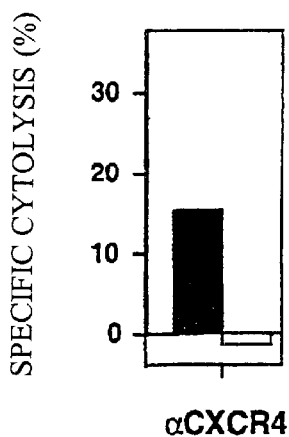
FIG. 3 shows the percent of specific cell death when incubated with anti-CXCR4 antibody.

BJAB cells are transfected with 2 μg of the hygromycin resistance vector pKEX2XL and 10 μg of the vector pCDM8-CD4 (Kolanus, University of Munich). Cell clones are selected in the presence of hygromycin B (450 U/ml). Select cell clones and BJAB cells, respectively, are also transfected with 10 μg of the vector pcDNA3-tag-CXCR4 (Moulard, University of Marseille). Cell clones are selected in the presence of G418 (4 mg/ml). Select cell clones of both transfection cycles are tested for the expression of the corresponding receptors. Cell clones which express CD4, CXCR4 or CD4 and CXCR4, are subjected to an apoptosis induction as described under (a) (cf. FIG. 2).

It shows that CD95-independent apoptosis can be induced in cells into which CD4 and/or CXCR4 has been introduced artificially.

II. Inhibition of CD95-independent Apoptosis

HPB-ALL cells are incubated with 250 nM SDF-1α at 37° C. for 30 minutes. The cells are then subjected to an apoptosis induction using the mouse anti-CXCR4 antibody (12G5), as described above under item I. (a).

It shows that the induction of cd95-independent apoptosis can be prevented by means of the artificial ligand of cxcr4, SDF-1α.

What is claimed is:

1. A method of inhibiting CD95-independent apoptosis, comprising the steps of:

(a) blocking the bonding of HIV-1 gp120 to receptors CD4 and/or with a competing factor for said bonding, and/or (b) inhibiting the signal path induced by the bonding of (a).

2. The method according to claim 1, wherein the competing factor is an anti-CD4 antibody.

3. The method according to claim 1, wherein the competing factor is an anti-CXCR4 antibody.

4. The method according to any one of claims 1 to 3, wherein (a) is blocked by a natural ligand of CD4 and/or a natural ligand of CXCR4.

5. The method of claim 4, wherein the natural ligand of CD4 is an MHC molecule.

6. The method according to claim 4, wherein the natural ligand of CXCR4 is SDF-1α.

7. A system for identifying substances suitable to inhibit CD95-independent apoptosis, comprising CD4+ and/or CXCR4+ cells, HIV-1 gp120, and a factor competing with HIV-1 gp120 for the bonding to CD4+ and/or CXCR4+.

8. The system according to claim 7, wherein the inhibitory effect of said factor is determined on the bonding of HIV-1 gp120 to receptors CD4 and/or CXCR4 or on the signal path induced by this bonding.

9. The system according to claim 7 or 8, wherein the factor is an anti-CD4 antibody.

10. The system according to claim 7 or 8, wherein the factor is an anti-CXCR4 antibody.

* * * * *